US012779230B2

(12) United States Patent
Block

(10) Patent No.: US 12,779,230 B2
(45) Date of Patent: Nov. 3, 2026

(54) SYSTEMS AND METHODS FOR ELECTRICAL SPATIAL FIELD FOR LEAD IMPLANT

(71) Applicant: Boston Scientific Neuromodulation Corporation, Valencia, CA (US)

(72) Inventor: Jessica Block, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 293 days.

(21) Appl. No.: 18/439,651

(22) Filed: Feb. 12, 2024

(65) Prior Publication Data

US 2025/0256110 A1 Aug. 14, 2025

Related U.S. Application Data

(60) Provisional application No. 63/445,079, filed on Feb. 13, 2023.

(51) Int. Cl.

*A61N 1/372* (2006.01)
*A61N 1/36* (2006.01)

(52) U.S. Cl.

CPC ..... *A61N 1/37241* (2013.01); *A61N 1/36062* (2017.08); *A61N 1/37247* (2013.01)

(58) Field of Classification Search

CPC ............ A61N 1/37241; A61N 1/36062; A61N 1/37247; A61N 1/0551; A61N 1/36185
See application file for complete search history.

(56) References Cited

U.S. PATENT DOCUMENTS 7,831,307 B1 * 11/2010 Moffitt ............... A61N 1/36185 607/46
8,483,836 B2 * 7/2013 Polefko .............. A61N 1/37247 607/46
8,666,506 B2 * 3/2014 King .................... A61N 1/0553 607/116
(Continued)

FOREIGN PATENT DOCUMENTS

AU 2012352009 A1 * 7/2014 ......... A61N 1/37264
AU 2014237614 A1 * 10/2015 ......... A61N 1/36128
(Continued)

*Primary Examiner* — David Hamaoui
*Assistant Examiner* — Haley N Pruitt
(74) *Attorney, Agent, or Firm* — Schwegman Lundberg & Woessner, P.A.

(57) ABSTRACT

A system may include a neural stimulator connected to at least one lead having a plurality of electrodes. The neural stimulator may be configured to store at least two preset programs, and to test each of the electrodes with equal amounts of cathodic energy by implementing at least two preset programs. Each of the preset programs may be configured to control delivery of neuromodulation to deliver neuromodulation energy using a different set of active electrodes from the plurality of electrodes. For each of the preset programs, the active electrodes may include at least two cathodic electrodes and at least two anodic electrodes, a total cathodic contribution for the neuromodulation energy may be evenly fractionalized across each of the at least two cathodic electrodes, and a total anodic contribution for the neuromodulation energy may be evenly fractionalized across each of the at least two anodic electrodes.

20 Claims, 13 Drawing Sheets

(56) References Cited

U.S. PATENT DOCUMENTS

| | | | | |
|---|---|---|---|---|
| 8,781,592 | B2 * | 7/2014 | Polefko | A61N 1/36017 607/46 |
| 11,198,012 | B2 * | 12/2021 | Cantua | A61N 1/37247 |
| 11,420,066 | B2 * | 8/2022 | Torgerson | A61N 1/36071 |
| 11,904,171 | B2 * | 2/2024 | Mustakos | A61N 1/36139 |
| 2005/0245987 | A1 * | 11/2005 | Woods | A61N 1/37247 607/46 |
| 2010/0057162 | A1 * | 3/2010 | Moffitt | A61N 1/0551 607/46 |
| 2011/0257707 | A1 * | 10/2011 | Kothandaraman | A61N 1/0551 607/60 |
| 2017/0348530 | A1 * | 12/2017 | Doan | A61N 1/36164 |
| 2018/0228547 | A1 * | 8/2018 | Parker | A61N 1/3605 |
| 2019/0148009 | A1 * | 5/2019 | Rao | A61N 1/36185 607/59 |
| 2019/0329040 | A1 * | 10/2019 | Mustakos | A61N 1/36189 |
| 2021/0387006 | A1 * | 12/2021 | Mustakos | A61N 1/36139 |
| 2022/0296902 | A1 * | 9/2022 | Zhang | A61N 1/0553 |
| 2023/0201596 | A1 * | 6/2023 | Zhang | A61B 5/4836 607/59 |

FOREIGN PATENT DOCUMENTS

| | | | | |
|---|---|---|---|---|
| AU | 2014233252 A1 | * | 11/2015 | A61N 1/37247 |
| CN | 106687174 A | * | 5/2017 | A61N 1/3616 |
| EP | 2752221 A2 | * | 7/2014 | A61N 1/3787 |

* cited by examiner

| ELECTRODE | 1ST CONFIG (1ST PRESET PROGRAM) | 2ND CONFIG (2ND PRESET PROGRAM) | 3RD CONFIG (3RD PRESET PROGRAM) | 4TH CONFIG (4TH PRESET PROGRAM) |
|---|---|---|---|---|
| 8 | -50 | | +50 | +50 |
| 7 | -50 | | +50 | +50 |
| 6 | | -50 | | |
| 5 | | -50 | | |
| 4 | | | -50 | |
| 3 | | | -50 | |
| 2 | +50 | +50 | | -50 |
| 1 | +50 | +50 | | -50 |

FIG. 12

| ELECTRODE | 1ST CONFIG (1ST PRESET PROGRAM) | 2ND CONFIG (2ND PRESET PROGRAM) | 3RD CONFIG (3RD PRESET PROGRAM) | 4TH CONFIG (4TH PRESET PROGRAM) |
|---|---|---|---|---|
| 8 | -50 | +25 | +25 | +34 |
| 7 | -50 | | +25 | +33 |
| 6 | | -50 | +25 | +33 |
| 5 | | -50 | | |
| 4 | | | -50 | |
| 3 | +33 | +25 | -50 | |
| 2 | +33 | +25 | | -50 |
| 1 | +34 | +25 | +25 | -50 |

FIG. 13

SYSTEMS AND METHODS FOR ELECTRICAL SPATIAL FIELD FOR LEAD IMPLANT

CLAIM OF PRIORITY

This application claims the benefit of U.S. Provisional Application No. 63/445,079 filed on Feb. 13, 2023, which is hereby incorporated by reference in its entirety.

TECHNICAL FIELD

This document relates generally to medical systems, and more particularly, but not by way of limitation, to systems, devices, and methods for testing lead implants to quickly and accurately assess if the lead(s) is (are) located close enough to the neural target to be successfully programmed.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes. SCS has conventionally used as a pain therapy, but may be implemented for other therapies as well.

Some neural targets may be complex structures with different types of nerve fibers. An example of such a complex structure is the neuronal elements in and around the spinal cord targeted by SCS. Furthermore, the number of available electrodes combined with the ability to generate a variety of complex electrical waveforms (e.g., pulses), presents a huge selection of modulation parameter sets to the clinician or patient. For example, if the neuromodulation system to be programmed has sixteen electrodes, millions of modulation parameter sets may be available for programming into the neuromodulation system.

SCS systems are implanted using a surgical procedure that places one or more leads near the spinal cord, and the neural stimulator is implanted under the skin. Although the SCS lead(s) have a plurality of electrodes that provide flexibility in programming the size, shape and location of the neuromodulation field, the lead(s) must still be appropriately positioned so that the neurostimulator can be programmed to deliver effective neuromodulation energy to the correct nerves for the desired therapy.

By way of example, the surgical procedure may take one to three hours which is a relatively long out-patient procedure. As it is a general goal to reduce the time and costs associated with surgical procedures, it is therefore desirable to minimize the implantation time to reduce the operating room time used for the procedure, as well as reduce the time of the physician, the device manufacturer rep, and the patient.

SUMMARY

An example (e.g., Example 1) of a system may include a neural stimulator connected to at least one lead having a plurality of electrodes. The neural stimulator may be configured to store at least two preset programs, and to test each of the plurality of electrodes with equal amounts of cathodic energy by implementing at least two preset programs. Each of the at least two preset programs may be configured to control delivery of neuromodulation to deliver neuromodulation energy using a different set of active electrodes from the plurality of electrodes. For each of the at least two preset programs, the active electrodes may include at least two cathodic electrodes and at least two anodic electrodes, a total cathodic contribution for the neuromodulation energy may be evenly fractionalized across each of the at least two cathodic electrodes, and a total anodic contribution for the neuromodulation energy may be evenly fractionalized across each of the at least two anodic electrodes.

In Example 2, the subject matter of Example 1 may optionally be configured such that the neural stimulator is configured to store four preset programs to test each of the plurality of electrodes with equal amounts of cathodic energy.

In Example 3, the subject matter of Example 2 may optionally be configured such that the at least one lead includes eight electrodes. The active electrodes in each of the four preset programs may include two cathodic electrodes where 50% of the total cathodic contribution for the neuromodulation energy is provided using each of the cathodic electrodes. Each of the four preset programs may include different cathodic electrodes than the other ones of the four preset programs.

In Example 4, the subject matter of Example 3 may optionally be configured such that the four preset programs include a first program configured to test electrode 1 and electrode 2 with 50% of the total cathodic contribution for the neuromodulation energy, a second program configured to test electrode 3 and electrode 4 with 50% of the total cathodic contribution for the neuromodulation energy, a third program configured to test electrode 5 and electrode 6 with 50% of the total cathodic contribution for the neuromodulation energy, and a fourth program configured to test electrode 7 and electrode 8 with 50% of the total cathodic contribution for the neuromodulation energy.

In Example 5, the subject matter of any one or more of Examples 3-4 may optionally be configured such that at least one of the four programs has two anodic electrodes. Fifty percent of the total anodic contribution for the neuromodulation energy may be provided using each of the two anodic electrodes.

In Example 6, the subject matter of any one or more of Examples 3-5 may optionally be configured such that at least one of the four programs has three anodic electrodes. About ⅓ of the total anodic contribution for the neuromodulation energy may be provided using each of the three anodic electrodes.

In Example 7, the subject matter of any one or more of Examples 3-6 may optionally be configured such that at least one of the four programs has four anodic electrodes. Twenty-five percent of the total anodic contribution for the neuromodulation energy may be provided using each of the four anodic electrodes.

In Example 8, the subject matter of Example 2 may optionally be configured such that the plurality of electrodes includes $N_T$ electrodes. The at least one lead may be one percutaneous lead with the $N_T$ electrodes on the one percutaneous lead, or may be two or more percutaneous leads with the $N_T$ electrodes equally distributed among the two or more percutaneous leads such that each of the two or more percutaneous leads have an equal number of electrodes, or may be a paddle lead with the $N_T$ electrodes arranged in rows and columns on the paddle lead. The active electrodes may include $N_C$ cathodic electrodes, where $N_C$ is $N_T/4$. The total cathodic contribution for the neuromodulation energy may be evenly fractionalized across each of the $N_C$ cathodic electrodes to deliver fractionalized cathodic energy $F_C$ to each of the $N_C$ cathodic electrodes, wherein $F_C=-100/N_C$.

In Example 9, the subject matter of Example 8 may optionally be configured such that the active electrodes include $N_A$ anodic electrodes. $N_A$ depends on a maximum cathodic electrode to anodic electrode spacing S corresponding to a number of electrodes that are not one of the $N_A$ anodic electrodes or one of the $N_C$ cathodic electrodes, where $S=N_T-(N_A+N_C)$.

In Example 10, the subject matter of Example 9 may optionally be configured to further include a programmer configured to program the neurostimulator with programs and to receive user input to adjust $N_A$, $N_C$ and S.

In Example 11, the subject matter of any one or more of Examples 9-10 may optionally be configured such that $N_A=N_C$ when S is $N_T/2$.

In Example 12, the subject matter of any one or more of Examples 9-11 may optionally be configured such that $N_A=N_C+(N_T/2-S)$ when S is less than $N_T/2$.

In Example 13, the subject matter of any one or more of Examples 9-12 may optionally be configured such that the programmer is configured to program the neuromodulator to replace at least one of the preset programs with at least one other program.

In Example 14, the subject matter of any one or more of Examples 9-13 may optionally be configured such that the neurostimulator is configured to implement the at least two preset programs one preset program at a time.

In Example 15, the subject matter of any one or more of Examples 9-14 may optionally be configured such that the neurostimulator is configured to implement at least two of the at least two preset programs concurrently.

Example 16 includes subject matter (such as a method, means for performing acts, machine readable medium including instructions that when performed by a machine cause the machine to perform acts, or an apparatus to perform). The subject matter may be used to identify effective placement of at least one lead having a plurality of electrodes, and may include testing each of the plurality of electrodes with equal amounts of cathodic energy by implementing at least two preset programs. Each of the at least two preset programs may be configured to control delivery of neuromodulation to deliver neuromodulation energy using a different set of active electrodes from the plurality of electrodes. For each of the at least two preset programs, the active electrodes may include at least two cathodic electrodes and at least two anodic electrodes, a total cathodic contribution for the neuromodulation energy may be evenly fractionalized across each of the at least two cathodic electrodes, and a total anodic contribution for the neuromodulation energy may be evenly fractionalized across each of the at least two anodic electrodes.

In Example 17, the subject matter of Example 16 may optionally be configured such that four preset programs are implemented to test each of the plurality of electrodes with the equal amounts of cathodic energy.

In Example 18, the subject matter of Example 17 may optionally be configured such that the at least one lead includes eight electrodes. The active electrodes in each of the four preset programs may include two cathodic electrodes where 50% of the total cathodic contribution for the neuromodulation energy is provided using each of the cathodic electrodes. Each of the four preset programs may include different cathodic electrodes than the other ones of the four preset programs.

In Example 19, the subject matter of Example 18 may optionally be configured such that the four preset programs include a first program configured to test electrode 1 and electrode 2 with 50% of the total cathodic contribution for the neuromodulation energy, a second program configured to test electrode 3 and electrode 4 with 50% of the total cathodic contribution for the neuromodulation energy, third program configured to test electrode 5 and electrode 6 with 50% of the total cathodic contribution for the neuromodulation energy, and a fourth program configured to test electrode 7 and electrode 8 with 50% of the total cathodic contribution for the neuromodulation energy.

In Example 20, the subject matter of Example 19 may optionally be configured such that the first program is configured to fractionalize 50% of the total anodic contribution to each of electrode 7 and electrode 8, the second program is configured to fractionalize 50% of the total anodic contribution to each of electrode 7 and electrode 8, the third program is configured to fractionalize 50% of the total anodic contribution to each of electrode 1 and electrode 2, and the fourth program is configured to fractionalize 50% of the total anodic contribution to each of electrode 1 and electrode 2.

In Example 21, the subject matter of Example 19 may optionally be configured such that the first program is configured to fractionalize about ⅓ of the total anodic contribution to each of electrode 6, electrode 7 and electrode 8, the second program is configured to fractionalize 25% of the total anodic contribution to each of electrode 1, electrode 6, electrode 7 and electrode 8, the third program is configured to fractionalize 25% of the total anodic contribution to each of electrode 1, electrode 2, electrode 3 and electrode 8, and the fourth program is configured to fractionalize about ⅓ of the total anodic contribution to each of electrode 1, electrode 2 and electrode 3.

In Example 22, the subject matter of Example 18 may optionally be configured such that at least one of the four programs has two anodic electrodes. Fifty percent of the total anodic contribution for the neuromodulation energy may be provided using each of the two anodic electrodes.

In Example 23, the subject matter of Example 18 may optionally be configured such that at least one of the four programs has three anodic electrodes. About ⅓ of the total anodic contribution for the neuromodulation energy may be provided using each of the three anodic electrodes.

In Example 25, the subject matter of any one or more of Examples 16-24 may optionally be configured such that the plurality of electrodes includes $N_T$ electrodes. The at least one lead may be one percutaneous lead with the $N_T$ electrodes on the one percutaneous lead, two or more percutaneous leads with the $N_T$ electrodes equally distributed among the two or more percutaneous leads such that each of the two or more percutaneous leads have an equal number of electrodes, or a paddle lead with the $N_T$ electrodes arranged in rows and columns on the paddle lead. The active electrodes may include $N_C$ cathodic electrodes, where $N_C$ is $N_T/4$. The total cathodic contribution for the neuromodulation energy may be evenly fractionalized across each of the $N_C$ cathodic electrodes to deliver fractionalized cathodic energy $F_C$ to each of the $N_C$ cathodic electrodes, wherein $F_C=-100/N_C$.

In Example 26, the subject matter of Example 25 may optionally be configured such that the active electrodes include $N_A$ anodic electrodes. $N_A$ may depend on a maximum cathodic electrode to anodic electrode spacing S corresponding to a number of electrodes that are not one of the $N_A$ anodic electrodes or one of the $N_C$ cathodic electrodes, where $S=N_T-(N_A+N_C)$.

In Example 27, the subject matter of Example 26 may optionally be configured such that $N_A$, $N_C$ and S are adjustable via user input.

In Example 28, the subject matter of Example 26 may optionally be configured such that $N_A=N_C$ when S is $N_T/2$.

In Example 29, the subject matter of Example 26 may optionally be configured such that $N_A=N_C+(N_T/2-S)$ when S is less than $N_T/2$.

In Example 30, the subject matter of any one or more of Examples 16-29 may optionally be configured such that the at least two preset programs are implemented one preset program at a time.

In Example 31, the subject matter of any one or more of Examples 16-29 may optionally be configured such that at least two of the at least two preset programs are concurrently implemented.

Example 32 includes subject matter (such as a non-transitory machine-readable medium including instructions, which when executed by a machine, cause the machine to perform a method for identifying effective placement of at least one lead having a plurality of electrodes) The method performed using the machine may include testing each of the plurality of electrodes with equal amounts of cathodic energy by implementing at least two preset programs. Each of the at least two preset programs may be configured to control delivery of neuromodulation to deliver neuromodulation energy using a different set of active electrodes from the plurality of electrodes. For each of the at least two preset programs, the active electrodes may include at least two cathodic electrodes and at least two anodic electrodes, a total cathodic contribution for the neuromodulation energy may be evenly fractionalized across each of the at least two cathodic electrodes, and a total anodic contribution for the neuromodulation energy may be evenly fractionalized across each of the at least two anodic electrodes.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 12 illustrates, by way of example and not limitation, fractionalizations for four preprogrammed configurations with two anodes used to test an implanted lead.

FIG. 13 illustrates, by way of example and not limitation, fractionalizations for four preprogrammed configurations more than with two anodes used to test an implanted lead.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to “an”, “one”, or “various” embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter enables a quick determination during an implantation procedure that SCS lead(s) are placed in a position that enables the lead(s) to stimulate the correct nerves for the therapy. For example, the present subject matter delivers a broad modulation field to determine if nerves can be captured, which eliminates the need to steer a narrower modulation field along the electrode array. It is noted that acute leads are implanted without the aid of a “can” electrode on the housing of an implantable device. For example, an implantable device with a can electrode may deliver a broad field using a cathodic electrode on the lead and an anodic can electrode as the return electrode. As the lead(s) are implanted without the use of an implanted can electrode, the present subject matter defines broad fields using the electrode array on the leads.

The present subject matter may provide predefined programs to provide a set of field shapes that prioritize excitation from the cathodic contacts, minimizes excitation from the anodic contacts, and spans the entire lead. Each of the set of fields shapes provide a broad field by positioning the anodes as far away from the cathodes as possible. No steering of the field is required as the field shapes are preset by the predefined programs. However, some embodiments may allow a user to move the broad field by clicking on the screen. In contrast to prior implantation procedures where a manufacturer's device rep remembers the electrode configuration that has coverage in order to program the implanted neuromodulator, the present subject matter may enable a user to save the electrode configuration that obtained adequate coverage using at least one of the predefined programs, which may serve as a starting point for additional sweet spot programming of the implanted neuromodulator to provide the desired therapy. The techniques of the present subject matter described herein may be used with either anterograde or retrograde lead placement.

Figure 1:
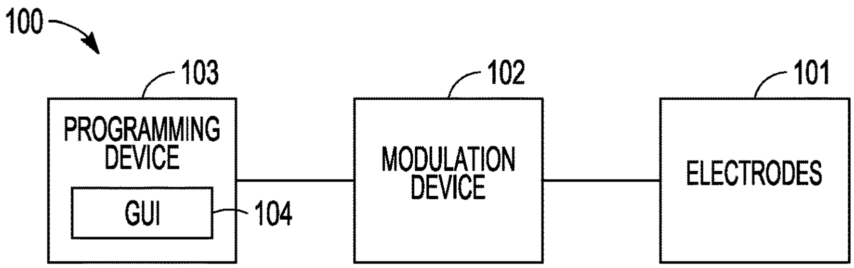
FIG. 1 illustrates, by way of example and not limitation, an embodiment of a neuromodulation system.

FIG. 1 illustrates, by way of example and not limitation, an embodiment of a neuromodulation system. The illustrated system 100 includes electrodes 101, a modulation device 102, and a programming system such as a programming device 103. The programming system may include multiple devices. The electrodes 101 are configured to be placed on or near one or more neural targets in a patient. The modulation device 102 is configured to be electrically connected to electrodes 101 and deliver neuromodulation energy, such as in the form of electrical pulses, to the one or more neural targets though electrodes 101. The delivery of the neuromodulation is controlled by using a plurality of modulation parameters. The modulation parameters may specify the electrical waveform (e.g., pulses or pulse patterns or other waveform shapes) and a selection of electrodes through which the electrical waveform is delivered. In various embodiments, at least some parameters of the plurality of modulation parameters are programmable by a user, such as a physician or other caregiver. The programming device 103 provides the user with accessibility to the user-programmable parameters. In various embodiments, the programming device 103 is configured to be communicatively coupled to modulation device via a wired or wireless link. In various embodiments, the programming device 103 includes a graphical user interface (GUI) 104 that allows the user to set and/or adjust values of the user-programmable modulation parameters.

Figure 2:
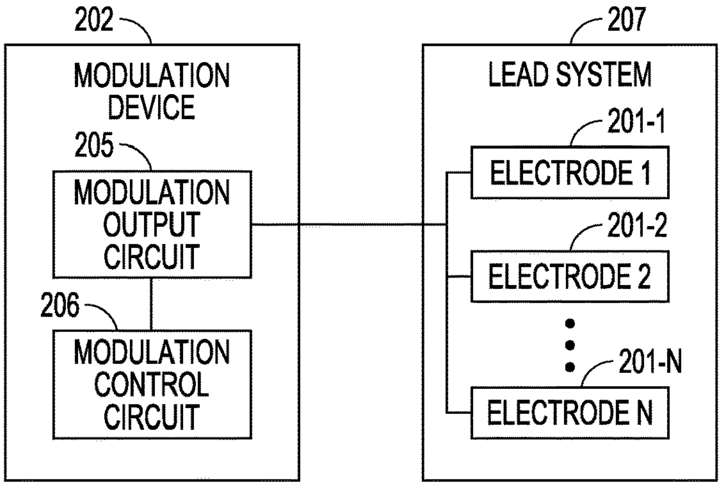
FIG. 2 illustrates an embodiment of a modulation device, such as may be implemented in the neuromodulation system of FIG. 1.

FIG. 2 illustrates an embodiment of a modulation device 202, such as may be implemented in the neuromodulation system 100 of FIG. 1. The illustrated embodiment of the modulation device 202 includes a modulation output circuit 205 and a modulation control circuit 206. Those of ordinary skill in the art will understand that the neuromodulation system may include additional components such as sensing circuitry for patient monitoring and/or feedback control of the therapy, telemetry circuitry and power. The modulation output circuit 205 produces and delivers the neuromodulation. Neuromodulation pulses are provided herein as an example. However, the present subject matter is not limited to pulses, but may include other electrical waveforms (e.g., waveforms with different waveform shapes, and waveforms with various pulse patterns). The modulation control circuit 206 controls the delivery of the neuromodulation pulses using the plurality of modulation parameters. The lead system 207 includes one or more leads each configured to be electrically connected to modulation device 202 and a plurality of electrodes 201-1 to 201-N distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 205 and tissue of the patient, where N≥2. The neuromodulation pulses are each delivered from the modulation output circuit 205 through a set of electrodes selected from the electrodes 201-1 to 201-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes a paddle lead.

The actual number and shape of leads and electrodes may vary for the intended application. An implantable waveform generator may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g., case electrode). The waveform generator may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by the waveform generator. Electrical modulation energy is provided to the electrodes in accordance with a set of modulation parameters programmed into the pulse generator. By way of example but not limitation, the electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the case of the waveform generator. The system may be capable of transmitting modulation energy to the tissue in a monopolar or multipolar (e.g., bipolar, tripolar, etc.) fashion. Monopolar modulation occurs when a selected one of the lead electrodes is activated along with the case of the waveform generator, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The waveform generator may be operated in a mode to deliver electrical modulation energy that is therapeutically effective and causes the patient to perceive delivery of the energy (e.g., therapeutically effective to relieve pain with perceived paresthesia), and may be operated in a sub-perception mode to deliver electrical modulation energy that is therapeutically effective and does not cause the patient to perceive delivery of the energy (e.g., therapeutically effective to relieve pain without perceived paresthesia). The waveform generator may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical waveforms (e.g., pulses), presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Figure 3:
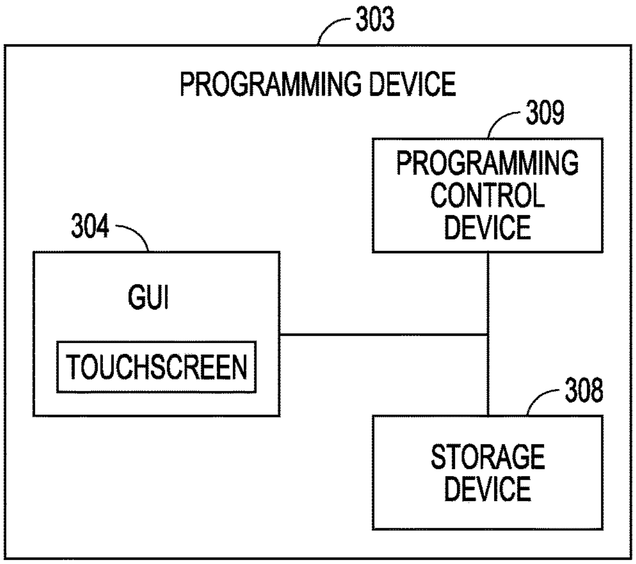
FIG. 3 illustrates an embodiment of a programming system such as a programming device, which may be implemented as the programming device in the neuromodulation system of FIG. 1.

FIG. 3 illustrates an embodiment of a programming system such as a programming device 303, which may be implemented as the programming device 103 in the neuromodulation system of FIG. 1. The programming device 303 includes a storage device 308, a programming control circuit 309, and a graphical user interface (GUI) 304. The programming control circuit 309 generates the plurality of modulation parameters that control the delivery of the neuromodulation pulses according to the pattern of the neuromodulation pulses. In various embodiments, the GUI 304 includes any type of presentation device, such as interactive or non-interactive screens, and any type of user input devices that allow the user to program the modulation parameters, such as touchscreen, keyboard, keypad, touchpad, trackball, joystick, and mouse. The storage device 308 may store, among other things, modulation parameters to be programmed into the modulation device. The programming device 303 may transmit the plurality of modulation parameters to the modulation device. In some embodiments, the programming device 303 may transmit power to the modulation device. The programming control circuit 309 may generate the plurality of modulation parameters. In various embodiments, the programming control circuit 309 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
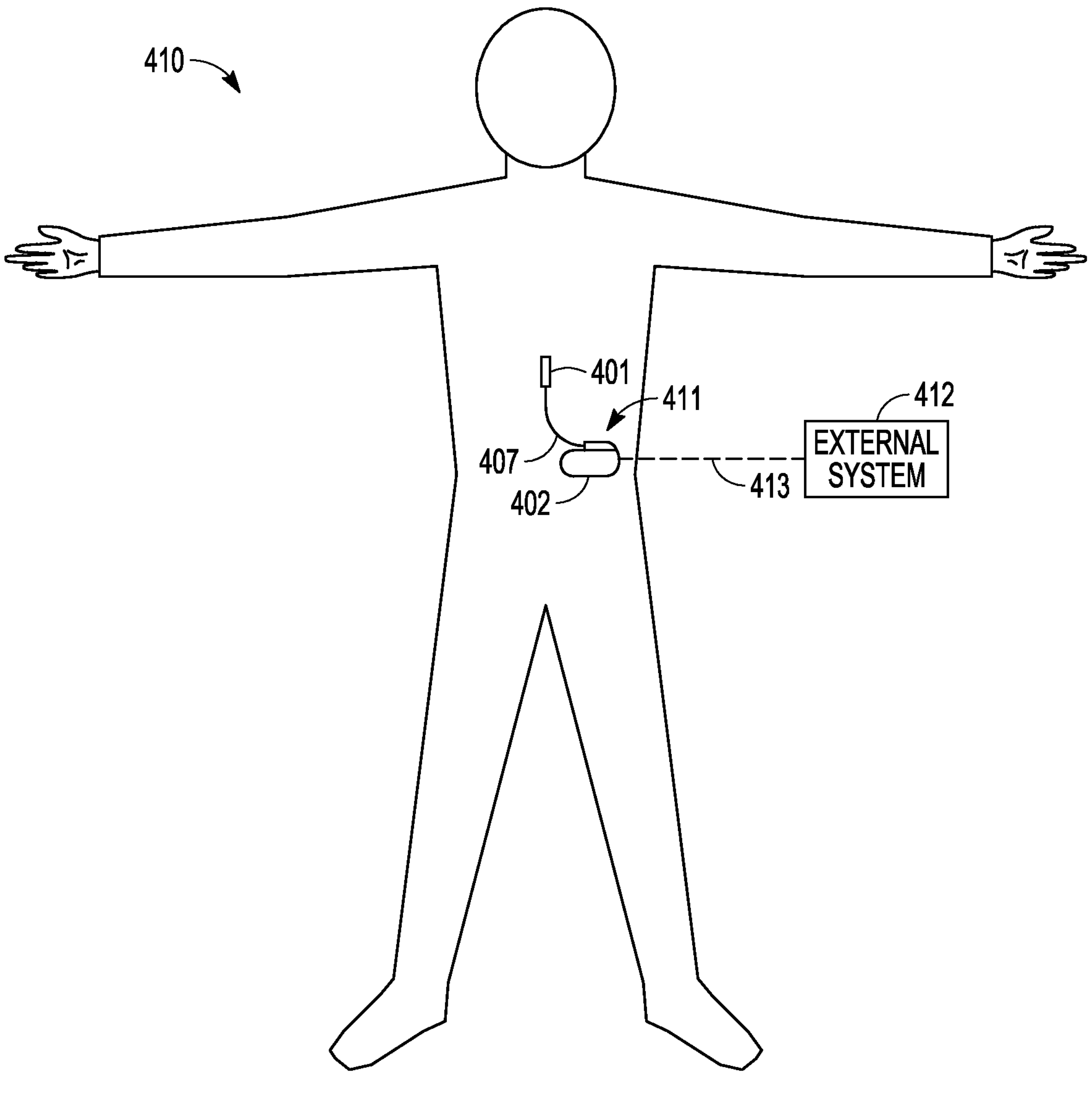
FIG. 4 illustrates, by way of example, an implantable neuromodulation system and portions of an environment in which system may be used.

FIG. 4 illustrates, by way of example, an implantable neuromodulation system and portions of an environment in which system may be used. The system is illustrated for implantation near the spinal cord. However, neuromodulation system may be configured to modulate other neural targets. The system 410 includes an implantable system 411, an external system 412, and a telemetry link 413 providing for wireless communication between implantable system 411 and external system 412. The implantable system is illustrated as being implanted in the patient's body. The implantable system 411 includes an implantable modulation device (also referred to as an implantable pulse generator, or IPG) 402, a lead system 407, and electrodes 401. The lead system 407 includes one or more leads each configured to be electrically connected to the modulation device 402 and a plurality of electrodes 401 distributed in the one or more leads. In various embodiments, the external system 412 includes one or more external (non-implantable) devices each allowing a user (e.g., a clinician or other caregiver and/or the patient) to communicate with the implantable system 411. In some embodiments, the external system 412 includes a programming device intended for a clinician or other caregiver to initialize and adjust settings for the implantable system 411 and a remote control device intended for use by the patient. For example, the remote control device may allow the patient to turn a therapy on and off and/or adjust certain patient-programmable parameters of the plurality of modulation parameters. The external system 412 may include personal devices such as phones and tablets.

The neuromodulation lead(s) of the lead system 407 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 402 may be implanted in a surgically-made pocket either in the abdomen or above the buttocks, or may be implanted in other locations of the patient's body. The lead extension(s) may be used to facilitate the implantation of the implantable modulation device 402 away from the exit point of the neuromodulation lead(s).

Figure 5:
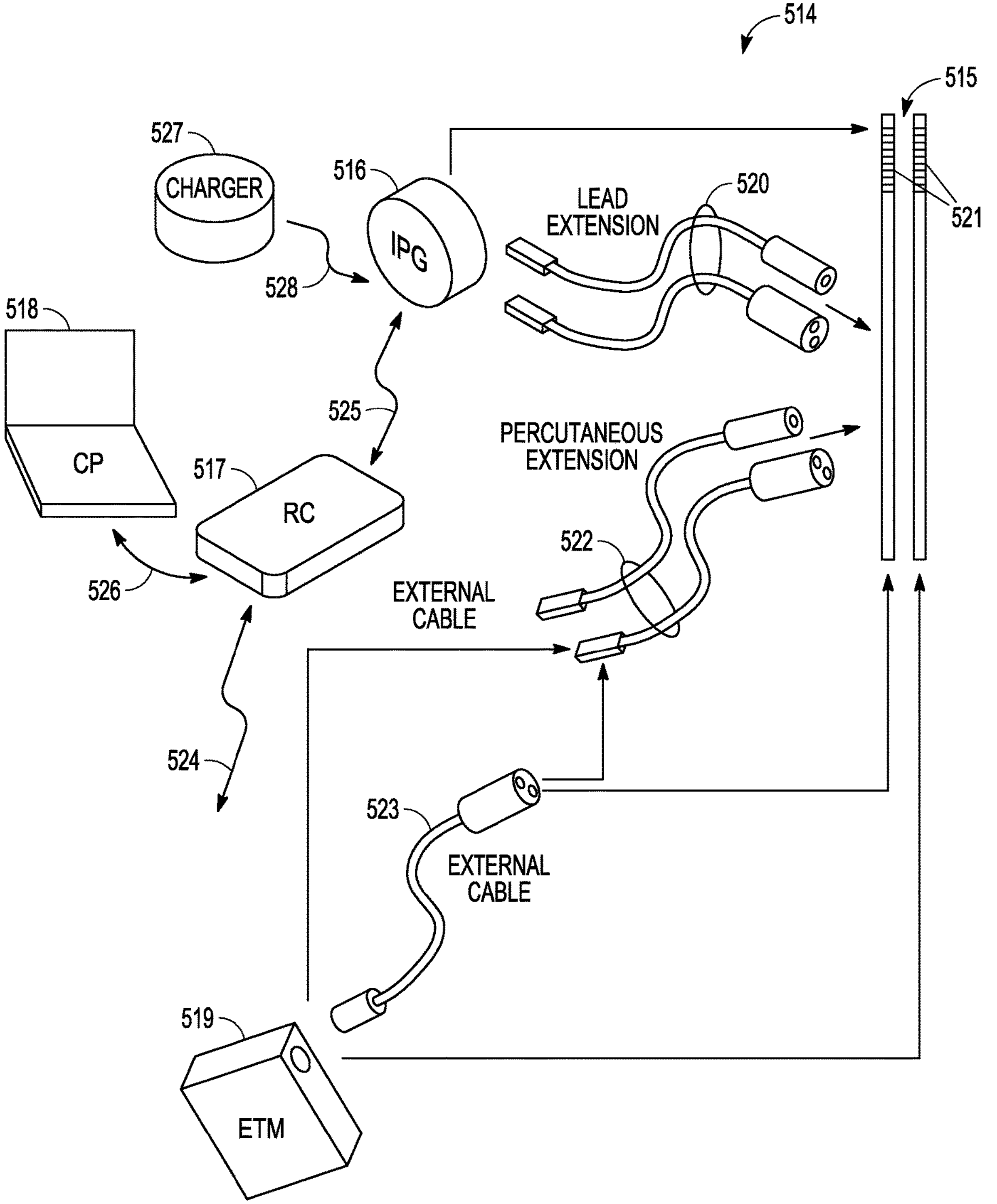
FIG. 5 illustrates, by way of example, an embodiment of a SCS system, which also may be referred to as a Spinal Cord Modulation (SCM) system.

FIG. 5 illustrates, by way of example, an embodiment of a SCS system, which also may be referred to as a Spinal Cord Modulation (SCM) system. The SCS system 514 may generally include one or more (illustrated as two) of implantable neuromodulation leads 515, an electrical waveform generator 516, an external remote controller (RC) 517, a clinician's programmer (CP) 518, and an external trial modulator (ETM) 519. IPGs are used herein as an example of the electrical waveform generator. However, it is expressly noted that the waveform generator may be configured to deliver regular, repeating patterns of pulses or in complex patterns that appear to be irregular patterns of pulses where pulses have differing amplitudes, pulse widths, pulse intervals, and bursts with differing number of pulses. It is also expressly noted that the waveform generator may be configured to deliver electrical waveforms other than pulses. The waveform generator 516 may be physically connected via one or more percutaneous lead extensions 520 to the neuromodulation leads 515, which carry a plurality of electrodes 521. As illustrated, the neuromodulation leads 515 may be percutaneous leads with the electrodes arranged in-line along the neuromodulation leads. Any suitable number of neuromodulation leads can be provided, including only one, as long as the number of electrodes is greater than two (including the waveform generator case function as a case electrode) to allow for lateral steering of the current. Alternatively, a surgical paddle lead can be used in place of one or more of the percutaneous leads. In some embodiments, the waveform generator 516 may include pulse generation circuitry that delivers electrical modulation energy in the form of a pulsed electrical waveform (i.e., a temporal series of electrical pulses) to the electrodes in accordance with a set of modulation parameters.

The ETM 519 may also be physically connected via the percutaneous lead extensions 522 and external cable 523 to the neuromodulation leads 515. The ETM 519 may have similar waveform generation circuitry as the waveform generator 516 to deliver electrical modulation energy to the electrodes accordance with a set of modulation parameters. The ETM 519 is a non-implantable device that is used on a trial basis after the neuromodulation leads 515 have been implanted and prior to implantation of the waveform generator 516, to test the responsiveness of the modulation that is to be provided. Functions described herein with respect to the waveform generator 516 can likewise be performed with respect to the ETM 519.

The RC 517 may be used to telemetrically control the ETM 519 via a bi-directional RF communications link 524. The RC 517 may be used to telemetrically control the waveform generator 516 via a bi-directional RF communications link 525. Such control allows the waveform generator 516 to be turned on or off and to be programmed with different modulation parameter sets. The waveform generator 516 may also be operated to modify the programmed modulation parameters to actively control the characteristics of the electrical modulation energy output by the waveform generator 516. A clinician may use the CP 518 to program modulation parameters into the waveform generator 516 and ETM 519 in the operating room and in follow-up sessions. The waveform generator 516 may be implantable. The implantable waveform generator 516 and the ETM 519 may have similar features as discussed with respect to the modulation device 202 described with respect to FIG. 2.

The CP 518 may indirectly communicate with the waveform generator 516 or ETM 519, through the RC 517, via an IR communications link 526 or other link. The CP 518 may directly communicate with the waveform generator 516 or ETM 519 via an RF communications link or other link (not shown). The clinician detailed modulation parameters provided by the CP 518 may also be used to program the RC 517, so that the modulation parameters can be subsequently modified by operation of the RC 517 in a stand-alone mode (i.e., without the assistance of the CP 518). Various devices may function as the CP 518. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 518. Alternatively, such programming methodologies can be performed using firmware or hardware. In any event, the CP 518 may actively control the characteristics of the electrical modulation generated by the waveform generator 516 to allow the desired parameters to be determined based on patient feedback or other feedback and for subsequently programming the waveform generator 516 with the desired modulation parameters. To allow the user to perform these functions, the CP 518 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g., CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant waveform generator, implant waveform generator and lead (s), replace waveform generator, replace waveform generator and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting.

An external charger 527 may be a portable device used to transcutaneously charge the waveform generator via a wireless link such as an inductive link 528. Once the waveform generator has been programmed, and its power source has been charged by the external charger or otherwise replenished, the waveform generator may function as programmed without the RC or CP being present.

Figure 6:
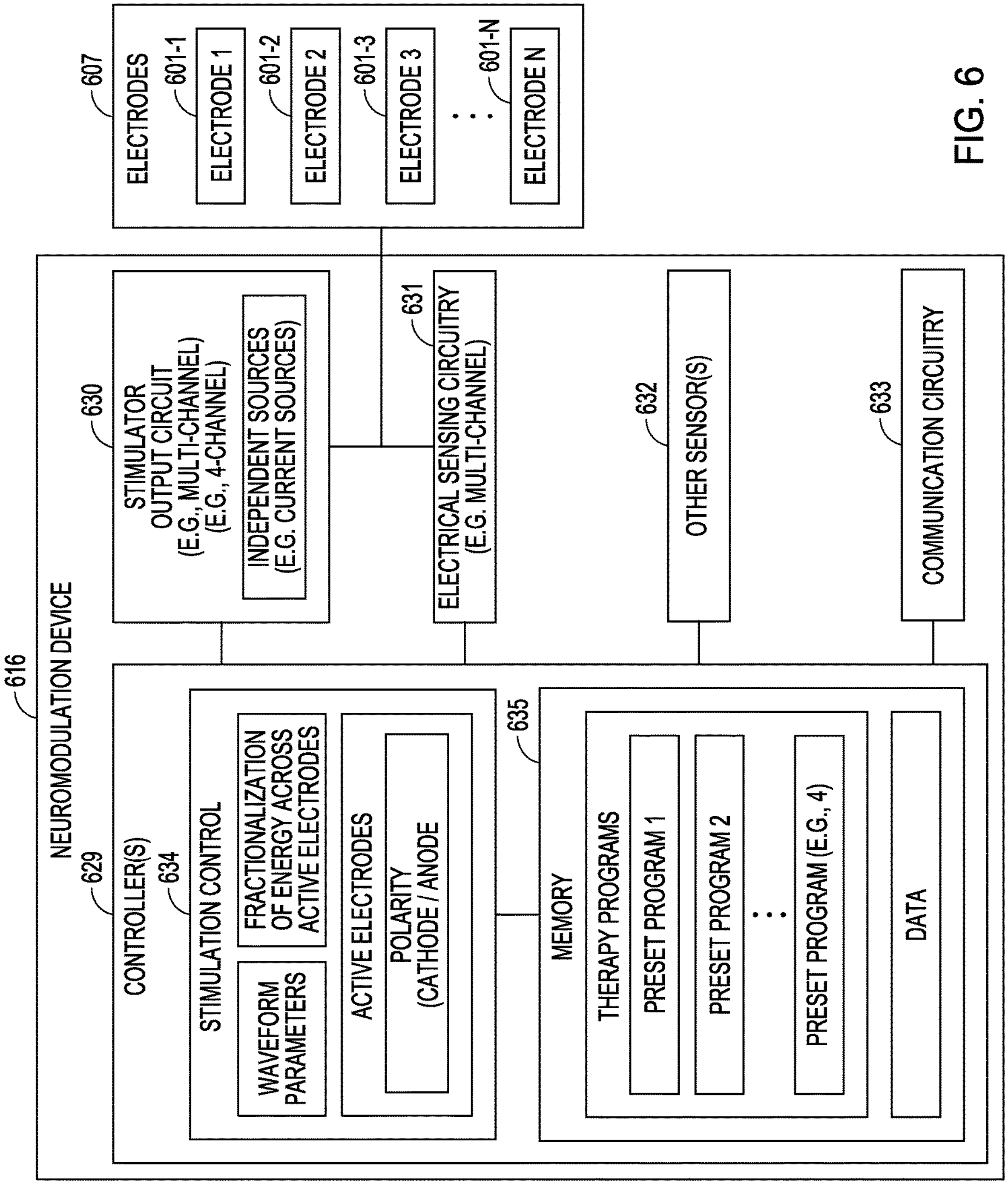
FIG. 6 illustrates, by way of example and not limitation, a neuromodulation device with preset programs for delivering neuromodulation.

FIG. 6 illustrates, by way of example and not limitation, a neuromodulation device with preset programs for delivering neuromodulation. The neuromodulation device 616 may correspond to the implantable waveform generator 516 and/or the ETM 519 in FIG. 5 or the modulation device 202 described with respect to FIG. 2. The neuromodulation device 616 may be connected to a lead system 607 which includes one or more leads each configured to be electrically connected to modulation device 602 and a plurality of electrodes 601-1 to 601-N distributed in an electrode arrangement using the one or more leads. The illustrated neuromodulation device 616 includes one or more controllers 629 operably connected to a stimulator output circuit 630 to deliver neuromodulation to the electrodes 607. The stimulator output circuit 630 may include a plurality of independent sources such as independent current sources for each electrode. The stimulator output circuit 630 may be configured as a multi-channel (e.g., 4 channel) system capable of simultaneously and independently generating and delivering separate stimulation waveforms to different electrode combinations. Some embodiments of the neuromodulation device 616 may include electrical sensing circuitry configured to sense electrical activity (e.g., evoked compound actions potentials or other electrical signs) using at least some of the electrodes. Some embodiments of the neuromodulation device 616 may include other sensor(s) 632 that may be used to control the neuromodulation or provide context for the therapy or other events. Some embodiments of the neuromodulation device 616 may include communication circuitry 633 used to communicate with at least one external device. The controller(s) 629 may be configured to provide stimulation control 634 to control the neuromodulation generated by the stimulator output circuit 630 and delivered to the electrodes 607, which may include the waveform parameters for the neuromodulation, the active electrodes and polarity of the active electrodes used to deliver the neuromodulation, and the fractionalization of energy across the active electrodes. The controller(s) 629 may include memory 635 configured to store data, and configured to store therapy programs. The therapy programs stored in the memory of the illustrated neuromodulation device 616 may include preset programs used to quickly determine that SCS lead(s) are placed in a position that enables the lead(s) to stimulate correct nerves for the therapy. For example, four preset programs may be stored. The four preset programs may correspond to four channels of the neuromodulator. The stored data in the memory 635 may include a variety of data used to deliver the therapy or evaluate the delivered therapy. By way of example and not limitation, the data may include sensor data or operational data (e.g., impedance, battery charge, etc.) for the device.

Various embodiments of the present subject matter may use these preset programs to quickly test whether the position of the electrodes is effective to deliver the desired therapy. Each of the preset programs may be configured to control delivery of neuromodulation to deliver neuromodulation energy using a different set of active electrodes from the plurality of electrodes. For each of the preset programs, the active electrodes may include at least two cathodic electrodes and at least two anodic electrodes. A total cathodic contribution for the neuromodulation energy may be evenly fractionalized across each of the at least two cathodic electrodes. A total anodic contribution for the neuromodulation energy may be evenly fractionalized across each of the at least two anodic electrodes. By way of example and not limitation, four preset programs may test each of the plurality of electrodes with equal amounts of cathodic energy.

Figure 7:
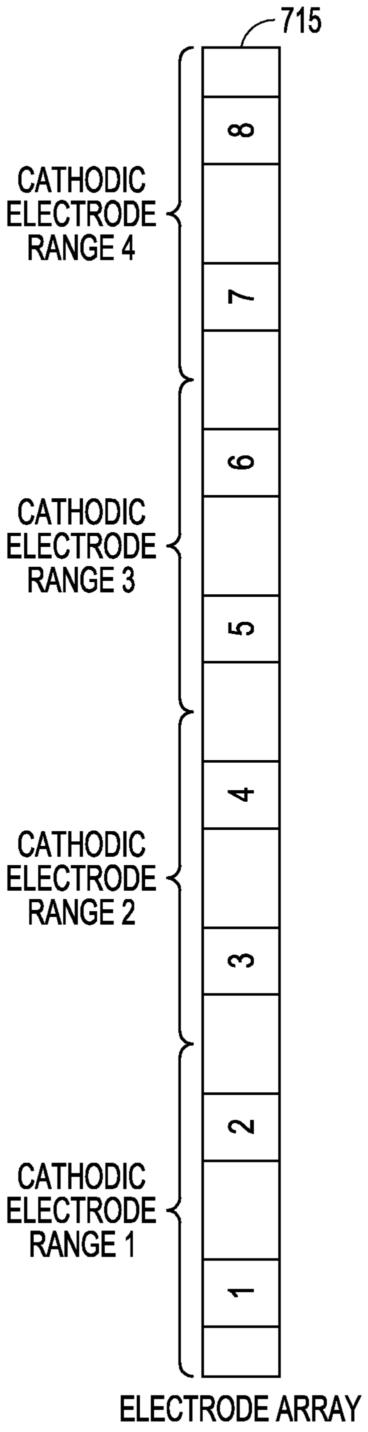
FIG. 7 illustrates, by way of example and not limitation, a linear array of electrodes on a single percutaneous lead.

FIG. 7 illustrates, by way of example and not limitation, a linear array of electrodes on a single percutaneous lead. The illustrated lead 715 includes eight electrodes. The illustrated electrodes are numbered 1 through 8, where the bottom electrode is numbered 1 and the top electrode is numbered 8. The numbering may be reversed for any of the illustrated leads where, instead of the numbering beginning at the bottom of the lead, the numbering begins at the top of the lead. The present subject matter may be implemented with anterograde or retrograde implantation techniques.

The electrodes may be divided into groups for use to test cathodic electrode ranges. In the illustrated embodiment, the eight electrodes may be divided into four groups to create four cathodic electrode ranges, identified as Cathodic Electrode Range 1, Cathodic Electrode Range 2, Cathodic Electrode Range 3, and Cathodic Electrode Range 4. Each range may provide equal cathodic contributions to each electrode in the range. For example, in the illustrated embodiment, each range includes two electrodes, such that 50% of the cathodic energy is provided to each of the two electrodes in the range. Thus, an equal amount of cathodic energy is tested for each electrode in the lead. If the range has three electrodes, then about ⅓ of the cathodic energy is provided to each of the three electrodes in the range, and if the range has n electrodes, then about 1/n of the cathodic energy is provided to each of the N electrodes in the range.

Figure 8:
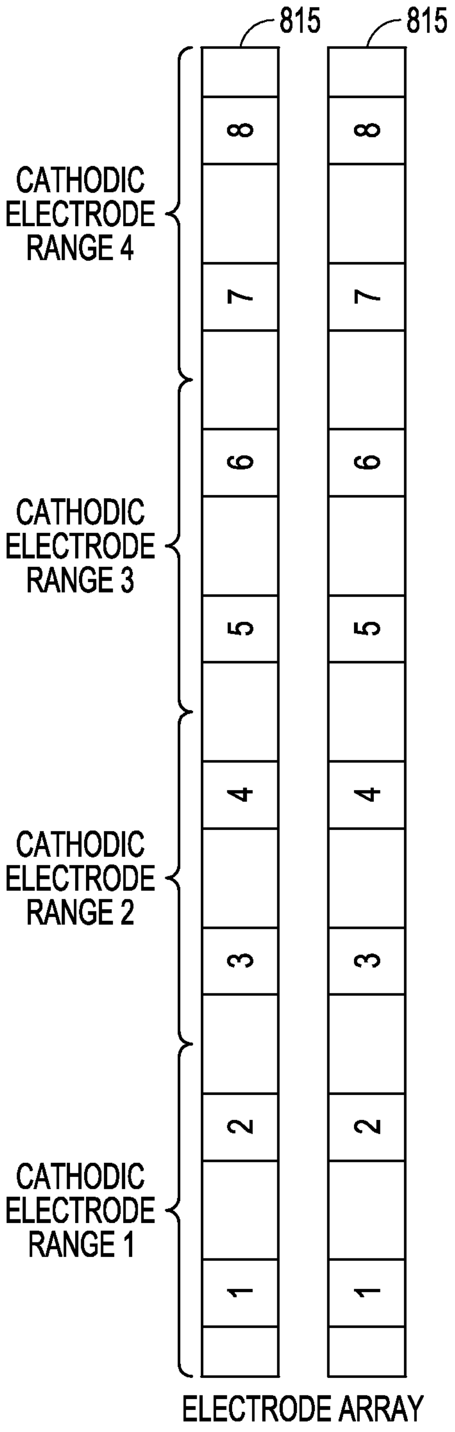
FIG. 8 illustrates, by way of example and not limitation, two percutaneous leads. Similar to FIG. 7, the electrodes in the two leads may be divided into groups for the purpose of testing cathodic electrode ranges.

FIG. 8 illustrates, by way of example and not limitation, two percutaneous leads. Similar to FIG. 7, the electrodes in the two leads 815 may be divided into groups for the purpose of testing cathodic electrode ranges. For example, cathodic electrode range 1 may include the first two electrodes (Electrodes 1 and 2) in each of the two leads, cathodic electrode range 2 may include Electrodes 3 and 4 in each of the two leads, and the like. Each range may provide equal cathodic contributions to each electrode in the range. For example, in the illustrated embodiment, each range includes four electrodes, such that 25% of the cathodic energy is provided to each of the two electrodes in the range. Thus, an equal amount of cathodic energy is tested for each electrode in the two leads.

Figure 9:
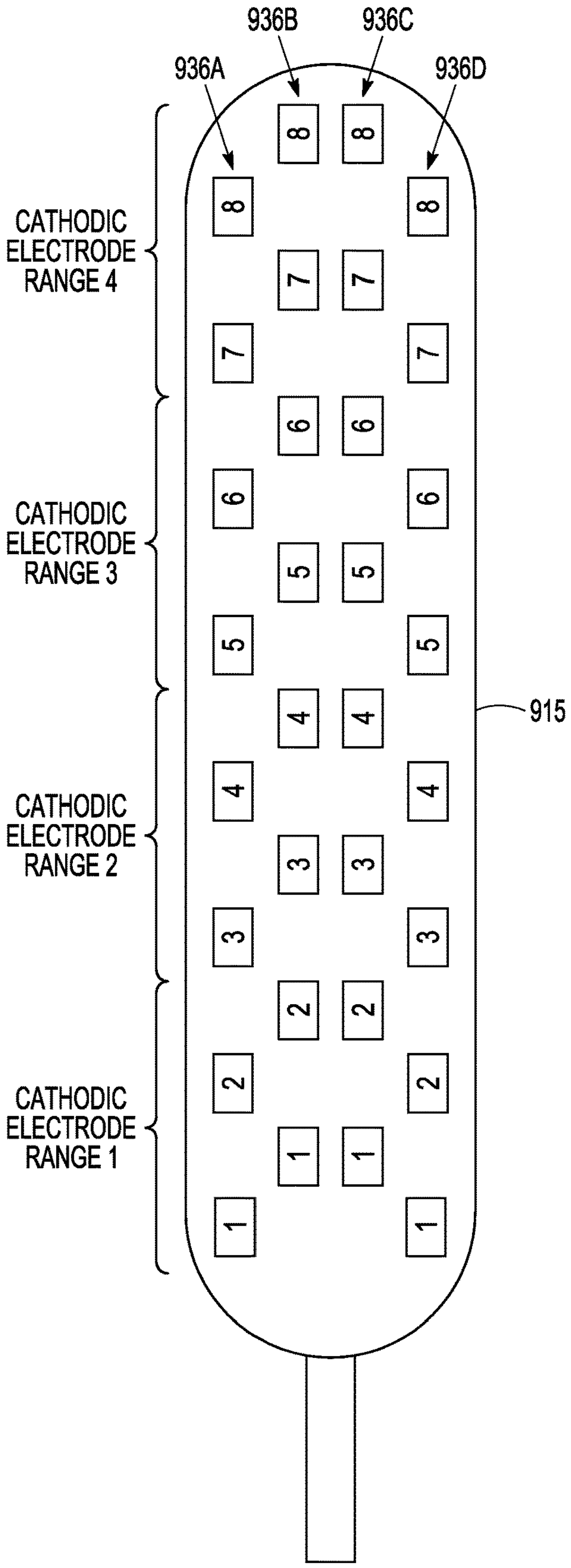
FIG. 9 illustrates, by way of example and not limitation, a paddle lead.

FIG. 9 illustrates, by way of example and not limitation, a paddle lead. The paddle lead 915 may include columns of electrodes. For example, the illustrated paddle lead includes four staggered columns 936A, 936B, 936C, 936D. In some embodiments, the paddle lead may include columns that are not staggered. Similar to FIGS. 7 and 8, the electrodes may be divided into groups for the purpose of testing cathodic electrode ranges. For example, cathodic electrode range 1 may include the first two electrodes (Electrodes 1 and 2) in each of the four columns 936A, 936B, 936C, 936D, cathodic electrode range 2 may include Electrodes 3 and 4 in each of the four columns 936A, 936B, 936C, 936D, and the like. Each range may provide equal cathodic contributions to each electrode in the range. For example, in the illustrated embodiment, each range includes eight electrodes, such that 12.5% of the cathodic energy is provided to each of the two electrodes in the range. Thus, an equal amount of cathodic energy is tested for each electrode in the two leads.

The present subject matter may be applied to a variety of lead designs with different electrodes. A brief generic discussion of the electrode configuration for the different lead configurations are provided below.

Figure 10:
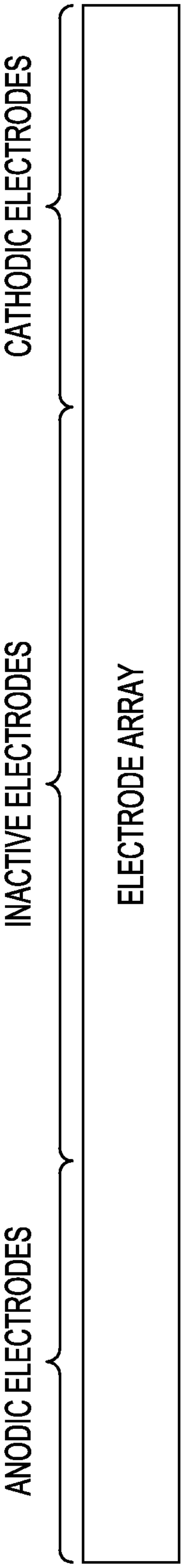
FIG. 10 illustrates, by way of example and not limitation, an electrode array with active and inactive electrodes.

FIG. 10 illustrates, by way of example and not limitation, an electrode array with active and inactive electrodes. The inactive electrodes are not used to deliver the neuromodulation field, and the active electrodes are selected for use to deliver the neuromodulation field. The selected active electrodes are defined to provide at least one anode and at least one cathode. By way of example and not limitation, the electrode array may include eight electrodes, where four electrodes are active and four electrodes are inactive. The four active electrodes may include two anodic electrodes and two cathodic electrodes. In order to provide a broad neuromodulation field, the anodic electrodes are separated from the cathodic electrodes as far as possible. In the illustrated electrode array, all of the inactive electrodes are between the anodic electrodes and the cathodic electrodes.

Figure 11:
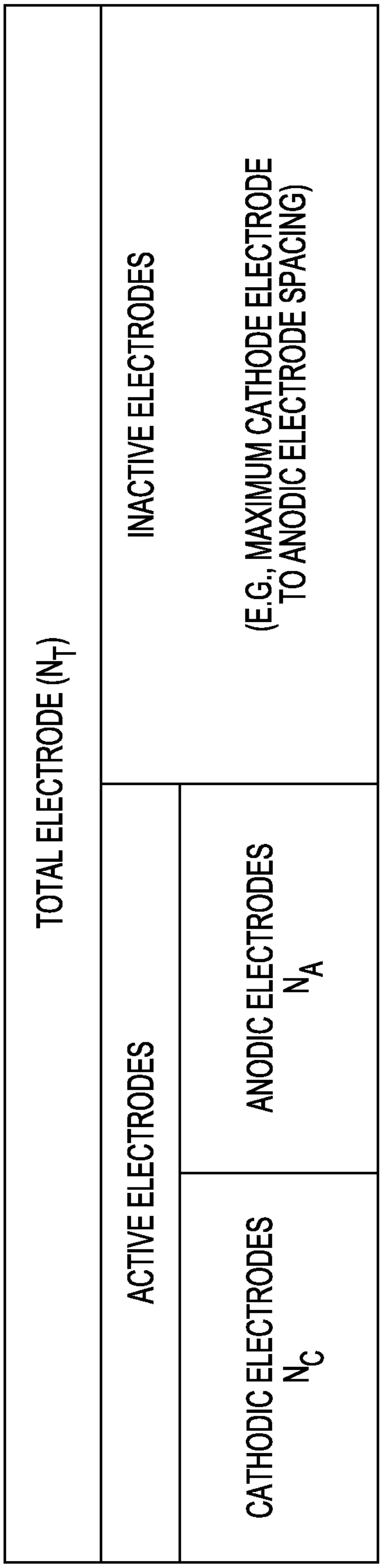
FIG. 11 illustrates a relationship between active and inactive electrodes, as well as cathodic and anodic electrodes, in an array of electrodes.

FIG. 11 illustrates a relationship between active and inactive electrodes, as well as cathodic and anodic electrodes, in an array of electrodes. The neuromodulation program may determine the active electrodes for use to deliver the neuromodulation from the total number of electrodes ($N_T$). The electrodes that are not used to deliver the neuromodulation are termed inactive electrodes. The neuromodulation program may determine the polarity of the active electrodes, including the number cathodic electrodes $N_C$ and the number of anodic electrodes $N_A$. The number of inactive electrodes determine the maximum spacing between cathodic electrodes and anodic electrodes. For example, as illustrated in FIG. 10, when testing cathodic electrodes at the end of an array, the anodic electrodes may be at the other end of the array and all of the inactive electrodes may be between the cathodic electrodes and the anodic electrodes Two or more preset programs may be used to test each of the plurality of electrodes with equal amounts of cathodic energy. Each of the preset programs is configured to control delivery of neuromodulation to deliver neuromodulation energy using a different set of active electrodes from the plurality of electrodes. The active electrodes in each preset program may include at least two cathodic electrodes and at least two anodic electrodes. A total cathodic contribution for the neuromodulation energy in each preset program may be evenly fractionalized across each of the at least two cathodic electrodes. A total anodic contribution for the neuromodulation energy in each preset program may be evenly fractionalized across each of the at least two anodic electrodes.

The total number of electrodes may be grouped together in each program to test more than one cathodic electrode in each program. The stimulation may be configured to deliver equal, or nearly equal, amounts of cathodic energy to each of the tested electrodes. Different embodiments may use a different number of present programs. A specific embodiment discussed herein uses four preset programs. In neurostimulation systems with four timing channels, the four preset programs may be independently implemented in the four timing channels, such that each timing channel is associated with a corresponding one of the present programs. Preset programs may be implemented sequentially or concurrently.

Therefore, by way of example and not limitation, four preset programs may be implemented to test each of the plurality of electrodes with the equal amounts of cathodic energy. The lead(s) may include eight electrodes. The active electrodes in each of the four preset programs may include two cathodic electrodes where 50% of the total cathodic contribution for the neuromodulation energy is provided using each of the cathodic electrodes. Each of the four preset programs may include different cathodic electrodes than the other ones of the four preset programs. The four preset programs may include a first program configured to test electrode 1 and electrode 2 with 50% of the total cathodic contribution for the neuromodulation energy, a second program configured to test electrode 3 and electrode 4 with 50% of the total cathodic contribution for the neuromodulation energy, a third program configured to test electrode 5 and electrode 6 with 50% of the total cathodic contribution for the neuromodulation energy, and a fourth program configured to test electrode 7 and electrode 8 with 50% of the total cathodic contribution for the neuromodulation energy.

The first program may be configured to fractionalize 50% of the total anodic contribution to each of electrode 7 and electrode 8, the second program is configured to fractionalize 50% of the total anodic contribution to each of electrode 7 and electrode 8, the third program is configured to fractionalize 50% of the total anodic contribution to each of electrode 1 and electrode 2, and the fourth program is configured to fractionalize 50% of the total anodic contribution to each of electrode 1 and electrode 2.

Some programs may be configured to use more than two anodes to distribute the anodic energy over more electrodes such that each anodic electrode has less anodic energy, which further minimizes potential excitation from anodic contacts. The first program may be configured to fractionalize about ⅓ of the total anodic contribution to each of electrode 6, electrode 7 and electrode 8, the second program may be configured to fractionalize 25% of the total anodic contribution to each of electrode 1, electrode 6, electrode 7 and electrode 8, the third program may be configured to fractionalize 25% of the total anodic contribution to each of electrode 1, electrode 2, electrode 3 and electrode 8, and the fourth program may be configured to fractionalize about ⅓ of the total anodic contribution to each of electrode 1, electrode 2 and electrode 3.

At least one of the four programs may have two anodic electrodes. Fifty percent of the total anodic contribution for the neuromodulation energy may be provided using each of the two anodic electrodes. At least one of the four programs may have three anodic electrodes. About ⅓ of the total anodic contribution for the neuromodulation energy may be provided using each of the three anodic electrodes.

More generally, the total number of electrodes may be $N_T$ electrodes distributed on one lead, on a plurality of leads, or on a paddle lead. The number of programs may be 4. The active electrodes for each program may include $N_C$ cathodic electrodes, where $N_C$ is $N_T/4$. The total cathodic contribution for the neuromodulation energy may be evenly fractionalized across each of the $N_C$ cathodic electrodes to deliver fractionalized cathodic energy $F_C$ to each of the $N_C$ cathodic electrodes, wherein $F_C=-100/N_C$. The active electrodes may include $N_A$ anodic electrodes. $N_A$ may depend on a maximum cathodic electrode to anodic electrode spacing S corresponding to a number of electrodes that are not one of the $N_A$ anodic electrodes or one of the $N_C$ cathodic electrodes, where $S=N_T-(N_A+N_C)$. $N_A$ may equal $N_C$ when S equals $N_T/2$, and $N_A$ may equal $N_C+(N_T/2-S)$ when S is less than $N_T/2$. Some embodiments provide a system that enable user input to selector or adjust at least some of $N_A$, $N_C$ and/or S.

The present programs may be implemented so that the preset programs are implemented one at a time (e.g., sequentially) to test each of the cathodic ranges in the electrode array. Two or more preset programs may be concurrently implemented using two or more channels. For example, the first and second program may be used to test half of the electrodes, and then the third and fourth program may be used to test the other half of the electrodes. The results may determine whether the first and second programs are separately tested or whether the third and fourth programs are separately tested to further identify the electrodes that are capable of capturing the targeted nerves.

FIG. 12 illustrates, by way of example and not limitation, fractionalizations for four preprogrammed configurations with two anodes used to test an implanted lead. By way of example, the illustrated table provides fractionalization values for each electrode in an 8-electrode lead. The tables may also represent fractionalization values for each row in an 8-row array of electrodes. The columns represent the four preset programs, where each program has a different stimulation configuration intended to test each of the electrodes with an equal amount of cathodic energy while providing a broad modulation field by separating the anodic electrodes as far as possible in the electrode array. Program 1 tests electrodes 7 and 8 with cathodic energy (50% each electrode), using electrodes 1 and 2 for the anodic energy (50% each electrode). Program 2 tests electrodes 5 and 6 with cathodic energy (50% each electrode), using electrodes 1 and 2 for the anodic energy (50% each electrode). Program 3 tests electrodes 3 and 4 with cathodic energy (50% each electrode), using electrodes 7 and 8 for the anodic energy (50% each electrode). Program 4 tests electrodes 1 and 2 with cathodic energy (50% each electrode), using electrodes 1 and 2 for the anodic energy (50% each electrode).

FIG. 13 illustrates, by way of example and not limitation, fractionalizations for four preprogrammed configurations more than with two anodes used to test an implanted lead. Spreading the anodic energy provides a broad field, and reduces the anodic energy near each of the anodes. There are more active electrodes than in FIG. 12, so there is less available spacing between the cathodic electrodes and anodic electrodes. By way of example, the illustrated table provides fractionalization values for each electrode in an 8-electrode lead. The tables may also represent fractionalization values for each row in an 8-row array of electrodes. The columns represent the four preset programs, where each program has a different stimulation configuration intended to test each of the electrodes with an equal amount of cathodic energy while providing a broad modulation field by separating the anodic electrodes as far as possible in the electrode array. Program 1 tests electrodes 7 and 8 with cathodic energy (50% each electrode), using electrodes 1, 2 and 3 for the anodic energy (33% or 34% for individual electrodes). Program 2 tests electrodes 5 and 6 with cathodic energy (50% each electrode), using electrodes 1, 2, 3 and 8 for the anodic energy (25% each electrode). Program 3 tests electrodes 3 and 4 with cathodic energy (50% each electrode), using electrodes 1, 6, 7 and 8 for the anodic energy (25% each electrode). Program 4 tests electrodes 1 and 2 with cathodic energy (50% each electrode), using electrodes 6, 7 and 8 for the anodic energy (33% or 34% for individual electrodes).

Figure 14:
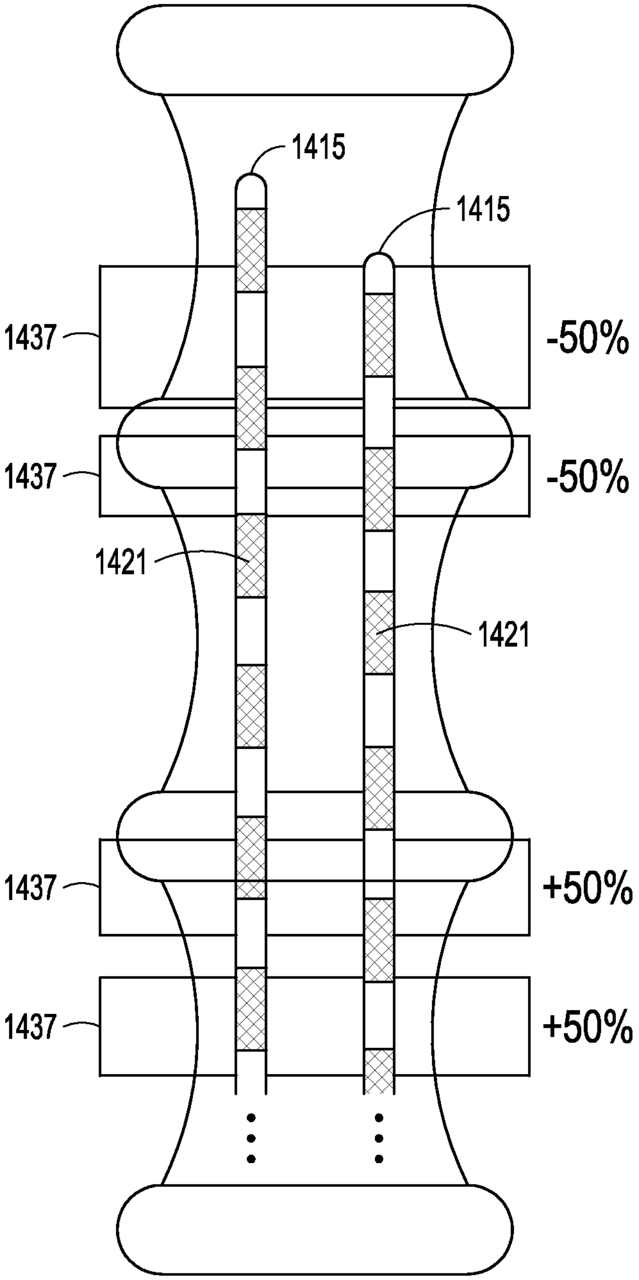
FIG. 14 illustrates, by way of example and not limitation, fractionalizations for two percutaneous leads.
Figure 15:
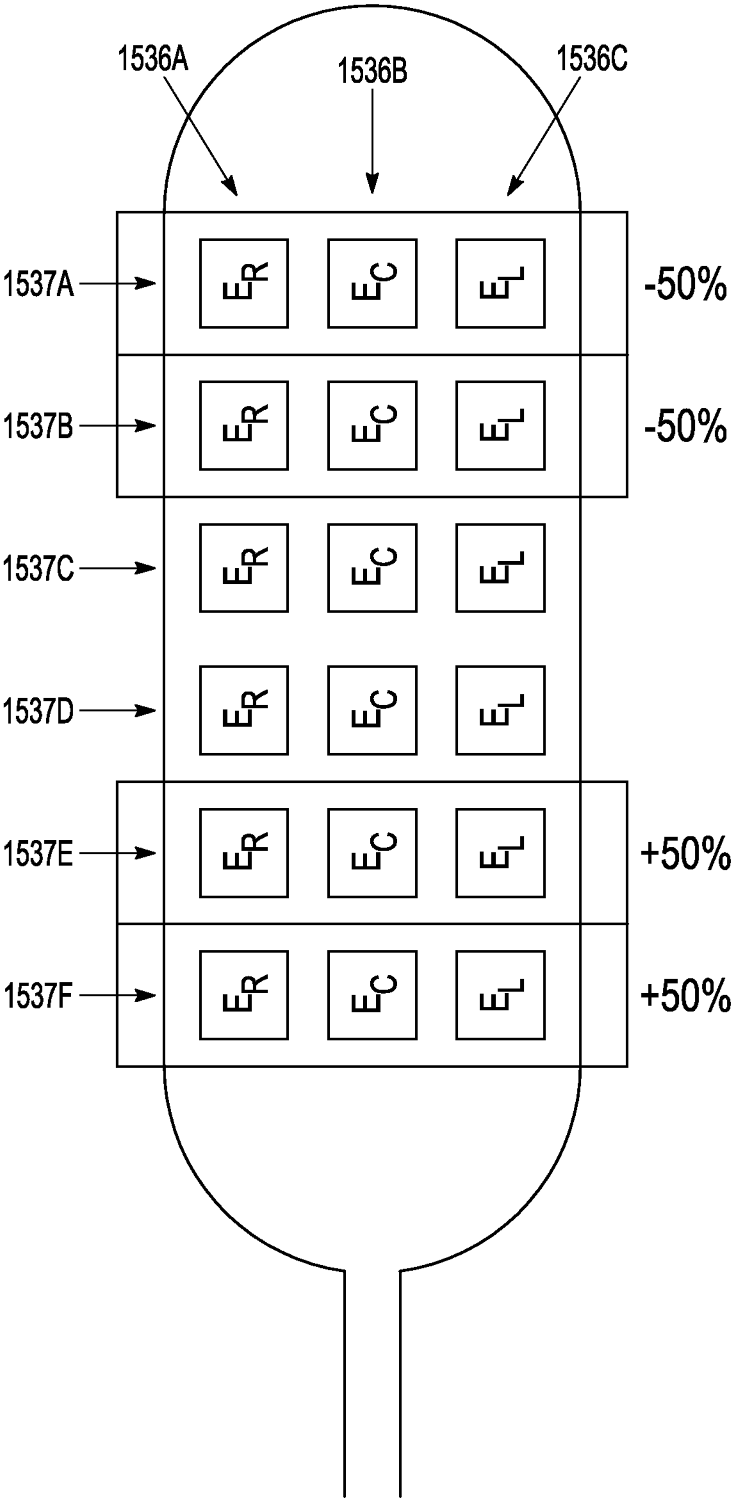
FIG. 15 illustrates, by way of example and not limitation, fractionalizations for a paddle lead.

FIG. 14 illustrates, by way of example and not limitation, fractionalizations for two percutaneous leads. The electrodes 1421 on each lead 1415 may serve as "rows" to be tested. Notably, the leads may be staggered. Yet, the corresponding electrodes on each lead 1415 may still be considered to be a row 1437 in an array of electrodes. Cathodic ranges may be tested as described above. FIG. 15 illustrates, by way of example and not limitation, fractionalizations for a paddle lead. The illustrated paddle lead 1515 includes three columns 1536A, 1536B, 1536C and six rows 1537A, 1537B, 1537C, 1537D, 1537E, 1537F of electrodes. The illustrated paddle lead has a similar configuration to the first preset program (column 1) in FIG. 12, but for FIG. 14 has six rows whereas FIG. 12 has eight electrodes (rows). Three preset programs may be used. A first program may test the first two rows 1537A, 1537B (e.g., bottom two rows 1537E, 1537F serving as anodes), the second program may test the middle two rows 1537C, 1537D (e.g., the top and bottom rows 1537A, 1537F serving as anodes), and the third program may test the bottom two rows 1537E, 1537F (e.g., the top two rows 1537A, 1537B serving as anodes).

Figure 16:
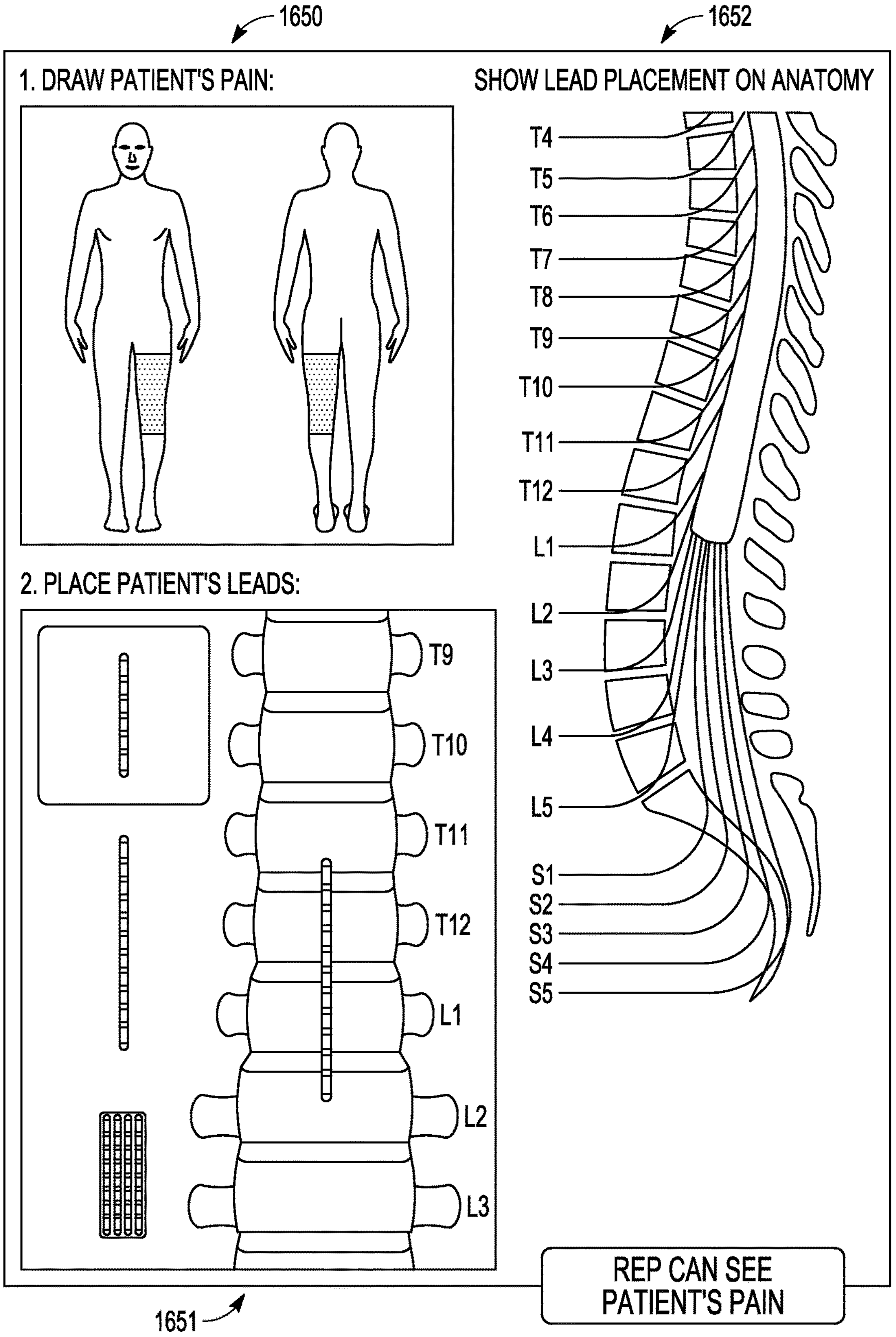
FIG. 16 illustrates, by way of example and not limitation, a display screen used during implantation.

FIG. 16 illustrates, by way of example and not limitation, a display screen used during implantation. The illustrated display screen includes a portion 1650 where the user may draw or otherwise identify the region of the patient's pain, a portion 1651 where the user can select a type of SCS lead, and place the lead on a representation of the patient's spinal anatomy, and a portion 1652 displaying a representation of the spinal anatomy and the lead placement, which allow the user (surgeon and/or device rep) to view the current lead placement with respect to the spinal anatomy during the implantation procedure. The preset programs may be delivered during the implantation to confirm if and where the neuromodulation is effective. This stimulation configuration may be saved, as used as a starting point for programming the implanted neuromodulator to deliver the desired therapy.

Figure 17:
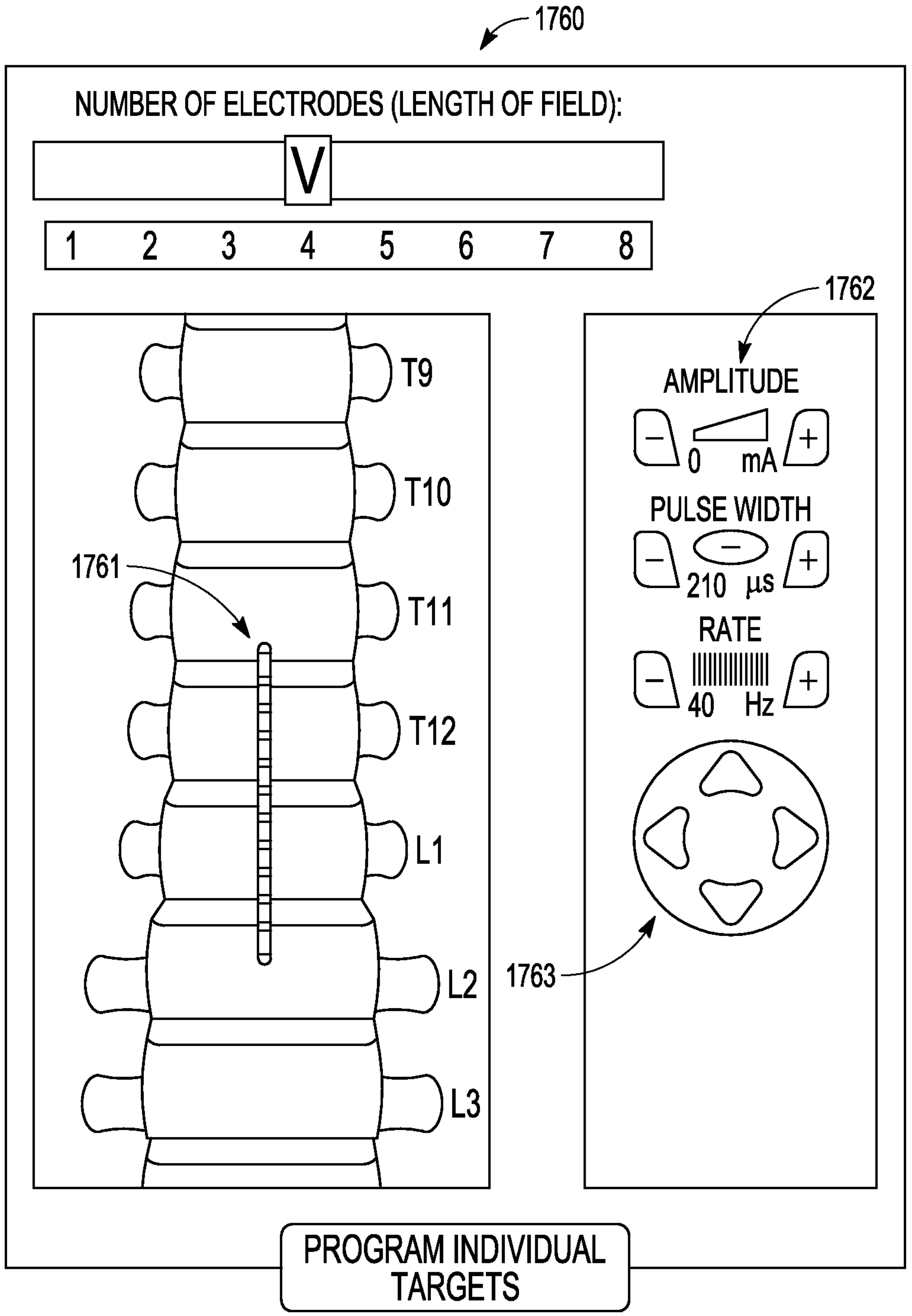
FIG. 17 illustrates, by way of example and not limitation, a programming screen used after implantation to program a neuromodulator.

FIG. 17 illustrates, by way of example and not limitation, a programming screen used after implantation to program a neuromodulator. The illustrated display includes a portion 1760 for selecting the number of active electrodes to be used for the modulation field, a portion 1761 identifying the selected active electrodes and/or modulation field generated by the fractionalized contributions of the active electrodes, and a portion 1762 for programming the amplitude, pulse width and frequency of the stimulation waveform, and a steering control 1763 to control the locus of the stimulation field by controlling the fractionalized contributions of various active electrodes.

Figure 18:
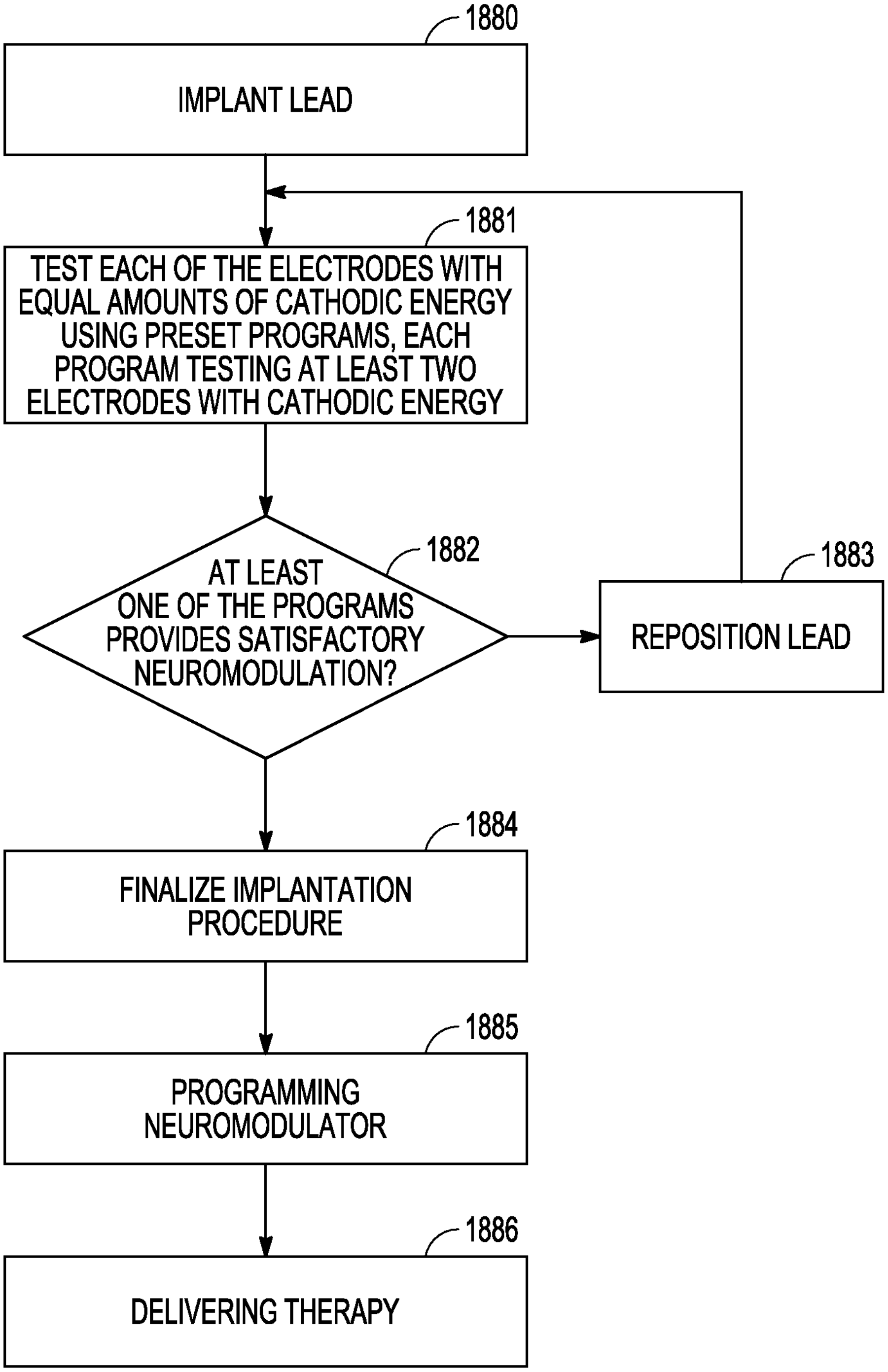
FIG. 18 illustrates, by way of example and not limitation, a method for implanting a lead(s) and programming neuromodulation using the implanted lead(s).

FIG. 18 illustrates, by way of example and not limitation, a method for implanting a lead(s) and programming neuromodulation using the implanted lead(s). The illustrated method includes implanting the lead(s) to position the leads a first position 1880. At 1881. each of the electrodes is tested with an equal amount of cathodic energy as the other electrodes using preset programs. Each program tests at least two of the electrodes on the lead(s). At 1882, it is determined whether at least one of the tested programs provides satisfactory neuromodulation for the anticipated therapy. For example, the surgeon may simply ask the patient is the patient is experiencing paresthesia that covers the area of the pain or is otherwise sensed to be effective for the therapy. Other system embodiments may include objective measure (s) s (e.g., sensor(s)) to determine if the stimulation is capturing the desired nerves. If none of the tested programs provide satisfactory neuromodulation, then the lead may be moved or repositioned to another position at 1883, and each of the programs may be tested again at 1881. If at least one of the tested programs provides satisfactory neuromodulation, then the implantation procedure may be finalized at 1884. An implanted neuromodulator may be programmed at 1885 to provide a sweet spot stimulation for the desired therapy. This process may involve both spatial adjustments to the modulation field by selecting appropriate active electrodes, polarities for the active electrodes, and fractionalize contributions for each polarity of the active electrodes. Spatial adjustments may also involve amplitude adjustments. This process may also involve temporal adjustments to the modulation field (e.g., adjustments to frequency, pulse width, burst duration, burst duty cycle, waveform shape, and pulse patterns (e.g., regular or irregular patterns of pulses).

A therapy may be delivered at 1886 using one or more programs saved in the implantable neuromodulator.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks or cassettes, removable optical disks (e.g., compact disks and digital video disks), memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method for identifying effective placement of at least one lead having a plurality of electrodes, the plurality of electrodes being divided into at least two electrode ranges each including two or more electrodes, the method comprising:

applying approximately equal amounts of cathodic energy to each of the plurality of electrodes by implementing at least two pre-stored preset programs, wherein each of the at least two pre-stored preset programs is configured to test a different one of the two or more electrode ranges, and wherein the at least two pre-stored preset programs collectively span the plurality of electrode ranges, wherein each of the at least two pre-stored preset programs is configured to control delivery of neuromodulation to deliver neuromodulation energy using a different set of active electrodes from the plurality of electrodes, wherein for each of the at least two pre-stored preset programs:

the active electrodes include at least two cathodic electrodes within the electrode range being tested and at least two anodic electrodes;

a total cathodic contribution for the neuromodulation energy is evenly fractionalized across each of the at least two cathodic electrodes; and a total anodic contribution for the neuromodulation energy is evenly fractionalized across each of the at least two anodic electrodes; and evaluating neuromodulation delivered by each of the at least two pre-stored preset programs to identify whether the at least one lead is effectively placed.

2. The method of claim 1, wherein four pre-stored preset programs are implemented to apply the approximately equal amounts of cathodic energy to each of the plurality of electrodes.

3. The method of claim 2, wherein the at least one lead includes eight electrodes divided into four electrode ranges each including two electrodes, and the active electrodes in each of the four pre-stored preset programs include two cathodic electrodes of the electrode range being tested by the preset program where 50% of the total cathodic contribution for the neuromodulation energy is provided using each of the cathodic electrodes, each of the four pre-stored preset programs including different cathodic electrodes than the other ones of the four pre-stored preset programs.

4. The method of claim 3, wherein the four pre-stored preset programs include:

a first program configured to test electrode 1 and electrode 2 with 50% of the total cathodic contribution for the neuromodulation energy;

a second program configured to test electrode 3 and electrode 4 with 50% of the total cathodic contribution for the neuromodulation energy;

a third program configured to test electrode 5 and electrode 6 with 50% of the total cathodic contribution for the neuromodulation energy; and a fourth program configured to test electrode 7 and electrode 8 with 50% of the total cathodic contribution for the neuromodulation energy.

5. The method of claim 4, wherein:

the first program is configured to fractionalize 50% of the total anodic contribution to each of electrode 7 and electrode 8;

the second program is configured to fractionalize 50% of the total anodic contribution to each of electrode 7 and electrode 8;

the third program is configured to fractionalize 50% of the total anodic contribution to each of electrode 1 and electrode 2; and the fourth program is configured to fractionalize 50% of the total anodic contribution to each of electrode 1 and electrode 2.

6. The method of claim 4, wherein:

the first program is configured to fractionalize about ⅓ of the total anodic contribution to each of electrode 6, electrode 7 and electrode 8;

the second program is configured to fractionalize 25% of the total anodic contribution to each of electrode 1, electrode 6, electrode 7 and electrode 8;

the third program is configured to fractionalize 25% of the total anodic contribution to each of electrode 1, electrode 2, electrode 3 and electrode 8; and the fourth program is configured to fractionalize about ⅓ of the total anodic contribution to each of electrode 1, electrode 2 and electrode 3.

7. The method of claim 3, wherein at least one of the four pre-stored preset programs has two anodic electrodes, wherein 50% of the total anodic contribution for the neuromodulation energy is provided using each of the two anodic electrodes.

8. The method of claim 3, wherein at least one of the four pre-stored preset programs has three anodic electrodes, wherein about ⅓ of the total anodic contribution for the neuromodulation energy is provided using each of the three anodic electrodes.

9. The method of claim 3, wherein at least one of the four pre-stored preset programs has four anodic electrodes, wherein 25% of the total anodic contribution for the neuromodulation energy is provided using each of the four anodic electrodes.

10. The method of claim 1, wherein:

the plurality of electrodes includes $N_T$ electrodes;

the at least one lead is:

one percutaneous lead with the $N_T$ electrodes on the one percutaneous lead;

two or more percutaneous leads with the $N_T$ electrodes equally distributed among the two or more percutaneous leads such that each of the two or more percutaneous leads have an equal number of electrodes; or a paddle lead with the $N_T$ electrodes arranged in rows and columns on the paddle lead;

the active electrodes include $N_C$ cathodic electrodes within the electrode range being tested, where $N_C$ is $N_T/4$; and the total cathodic contribution for the neuromodulation energy is evenly fractionalized across each of the $N_C$ cathodic electrodes to deliver fractionalized cathodic energy $F_C$ to each of the $N_C$ cathodic electrodes, wherein $F_C=-100/N_C$.

11. The method of claim 10, wherein the active electrodes include $N_A$ anodic electrodes, wherein $N_A$ depends on a maximum cathodic electrode to anodic electrode spacing S corresponding to a number of inactive electrodes that are not one of the $N_A$ anodic electrodes or one of the $N_C$ cathodic electrodes and that are positioned between the N_C cathodic electrodes and the N_A anodic electrodes, where $S=N_T-(N_A+N_C)$.

12. The method of claim 11, wherein $N_A$, $N_C$ and S are adjustable via user input.

13. The method of claim 11, wherein $N_A=N_C$ when S is $N_T/2$.

14. The method of claim 11, wherein $N_A=N_C+(N_T/2-S)$ when S is less than $N_T/2$.

15. The method of claim 1, wherein the at least two pre-stored preset programs are implemented one preset program at a time.

16. The method of claim 1, wherein at least two of the at least two pre-stored preset programs are concurrently implemented.

17. A non-transitory machine-readable medium including instructions, which when executed by a machine, cause the machine to perform a method at least one lead having a plurality of electrodes divided into a plurality of electrode ranges each including two or more electrodes, the method comprising:

applying approximately equal amounts of cathodic energy to each of the plurality of electrodes by implementing at least two pre-stored preset programs, wherein each of the at least two pre-stored preset programs is configured to test a different one of the plurality of electrode ranges, and wherein the at least two pre-stored preset programs collectively span the plurality of electrode ranges, wherein each of the at least two preset programs is configured to control delivery of neuromodulation to deliver neuromodulation energy using a different set of active electrodes from the plurality of electrodes, wherein for each of the at least two pre-stored preset programs:

the active electrodes include at least two cathodic electrodes within the electrode range being tested and at least two anodic electrodes;

a total cathodic contribution for the neuromodulation energy is evenly fractionalized across each of the at least two cathodic electrodes; and a total anodic contribution for the neuromodulation energy is evenly fractionalized across each of the at least two anodic electrodes.

18. A system, comprising:

a neural stimulator connected to at least one lead having a plurality of electrodes divided into a plurality of electrode ranges each including two or more electrodes, wherein the neural stimulator is configured to store at least two pre-stored preset programs, and to apply approximately equal amounts of cathodic energy to each of the plurality of electrodes by implementing the at least two pre-stored preset programs, wherein each of the at least two preset programs is configured to test a different one of the plurality of electrode ranges, and wherein the at least two pre-stored preset programs collectively span the plurality of electrode ranges, wherein each of the at least two pre-stored preset programs is configured to control delivery of neuromodulation to deliver neuromodulation energy using a different set of active electrodes from the plurality of electrodes, wherein for each of the at least two preset programs:

the active electrodes include at least two cathodic electrodes within the electrode range being tested and at least two anodic electrodes;

a total cathodic contribution for the neuromodulation energy is evenly fractionalized across each of the at least two cathodic electrodes; and a total anodic contribution for the neuromodulation energy is evenly fractionalized across each of the at least two anodic electrodes.

19. The system of claim 18, wherein:

the neural stimulator is configured to store four pre-stored preset programs to apply the approximately equal amounts of cathodic energy to each of the plurality of electrodes;

the at least one lead includes eight electrodes divided into four electrode ranges each including two electrodes; and the active electrodes for each of the four pre-stored preset programs include two cathodic electrodes of the electrode range being tested by the preset program where 50% of the total cathodic contribution for the neuromodulation energy is provided using each of the cathodic electrodes, each of the four pre-stored preset programs including different cathodic electrodes than the other ones of the four pre-stored preset programs.

20. The system of claim 18, wherein the four present preset programs include:

a first program configured to test electrode 1 and electrode 2 with 50% of the total cathodic contribution for the neuromodulation energy;

a second program configured to test electrode 3 and electrode 4 with 50% of the total cathodic contribution for the neuromodulation energy;

a third program configured to test electrode 5 and electrode 6 with 50% of the total cathodic contribution for the neuromodulation energy; and a fourth program configured to test electrode 7 and electrode 8 with 50% of the total cathodic contribution for the neuromodulation energy.

* * * * *